United States Patent [19]

Fischell et al.

[11] Patent Number: 4,765,332
[45] Date of Patent: Aug. 23, 1988

[54] PULLBACK ATHERECTOMY CATHETER SYSTEM

[75] Inventors: Robert E. Fischell, Silver Spring, Md.; Tim A. Fischell, Palo Alto, Calif.

[73] Assignee: MedInnovations, Inc., Dayton, Md.

[21] Appl. No.: 885,139

[22] Filed: Jul. 14, 1986

[51] Int. Cl.[4] .............................................. A61B 17/32
[52] U.S. Cl. .................................... 128/305; 128/304
[58] Field of Search ................... 128/24 A, 305, 304, 128/328; 604/22, 267, 268, 264

[56] References Cited

U.S. PATENT DOCUMENTS

| | | | |
|---|---|---|---|
| 1,167,014 | 1/1916 | O'Brien | 128/305 |
| 1,628,275 | 5/1927 | Robinson | 128/304 |
| 2,730,101 | 1/1956 | Hoffman | 128/305 |
| 3,472,230 | 10/1969 | Fogarty | 128/304 |
| 3,565,062 | 2/1971 | Kuris | 128/303 R |
| 3,764,427 | 10/1973 | Reimels | 128/304 |
| 3,831,585 | 8/1974 | Brondy et al. | 128/328 |
| 4,027,658 | 6/1977 | Marshall | 128/304 |
| 4,055,167 | 10/1977 | Bernstein | 128/304 |
| 4,243,049 | 1/1981 | Goodale et al. | 128/304 |
| 4,273,128 | 6/1981 | Lary | 128/344 |
| 4,559,927 | 12/1985 | Chin | 128/304 |
| 4,589,412 | 5/1986 | Kensey | 604/22 |
| 4,627,436 | 12/1986 | Leckrone | 128/303.1 |
| 4,631,052 | 12/1986 | Kensey | 604/22 |

FOREIGN PATENT DOCUMENTS 2044103 10/1980 United Kingdom ............... 128/304

*Primary Examiner*—C. Fred Rosenbaum
*Assistant Examiner*—Gene B. Kartchner
*Attorney, Agent, or Firm*—Howard W. Califano

[57] ABSTRACT

An atherectomy apparatus and method is disclosed for the purpose of surgical excision of atheromas which typically consist of plaque deposits that cause narrowing (stenosis) of an artery. The apparatus, called a pullback atherectomy catheter, cuts and collects obstructive material into a collection chamber as the catheter is pulled back through obstructive material within a human vessel such as an artery.

36 Claims, 2 Drawing Sheets

PULLBACK ATHERECTOMY CATHETER SYSTEM

FIELD OF THE INVENTION

This invention is in the field of percutaneous transluminal arterial catheters which are designed for the purpose of surgical excision of atheromas which typically consist of plaque deposits that cause narrowing (stenosis) of an artery. The cutting out of atheromas has been given the name "atherectomy".

BACKGROUND OF THE INVENTION

Atherosclerotic arterial disease is the leading cause of morbidity and mortality in the United States and most other developed countries. Atherosclerosis is a chronic disease process characterized by lipid deposits and fibrosis of the intima, irregularly distributed in large and medium sized arteries. The disease is progressive and most often becomes clinically manifest in the middle-aged and elderly. When severe, the atheroschlerotic plaque causes a reduction of the cross-sectional area of the arterial lumen, with and without thrombosis. Resultant ischemic manifestations include: angina pectoris, myocardial infarction, stroke, intermittent claudication, gangrene of the lower extremities and renovascular hypertension.

The current management of atherosclerotic disease includes preventative therapy aimed at minimizing known major risk factors such as hypertension, smoking, hypercholesterolemia and diabetes mellitus.

Coronary artery bypass grafting (CABG), carotid endarterectomy and bypass grafting (autogenous vein or synthetic graft) of the iliac, femoral and renal arteries are all well established surgical methods of palliative therapy. Although these procedures are often effective in relieving ischemia, each of these represents a major surgical operation with significant associated morbidity, mortality and expense. CABG, for example, requires the opening of the chest cavity (thoracotomy) and use of cardiopulmonary bypass, with not uncommon postoperative complications including postpericardotomy syndrome, Non-A Non-B hepatitis, stroke and a mortality of approximately one percent (1%) at most medical centers.

Percutaneous transluminal angioplasty (PTA) by means of a balloon catheter is a relatively new ("non-surgical") procedure with proven efficacy in relief of atheroschlerotic obstruction of the coronary, renal and peripheral circulations. The technique involves the percutaneous passage (under local anesthesia) of a specialized balloon-tipped catheter through the site of arterial narrowing, and inflation of the balloon to reduce obstruction. This is always done in conjunction with angiographic visualization of the vessel being treated. When successful, this procedure results in a reduction of the arterial stenosis and a decrease in the transstenotic pressure gradient. The mechanism of action is felt to consist of some combination of plaque compression, intimal splitting and medial/adventitial stretching. Healing of the balloon-damaged plaque may involve fibrosis and retraction of the split intimal elements, with further luminal enlargement in the weeks to months following the procedure.

The safety and efficacy of PTA is a function of the vessel being treated, patient selection, and the expertise of the physician performing the procedure. Primary angiographic success, defined as 20% or greater reduction of stenosis, is now achieved in approximately 80–90% of attempts in carefully selected patients at experienced centers. The obvious advantage of PTA, compared to surgical palliative therapy, is that it does not require major surgery or general anesthesia with the associated sequelae.

Despite its proven efficacy in the palliation of obstructive atherosclerotic disease, PTA, as it is currently performed, has several important technical limitations. These limitations are particularly true in the application of PTA to the coronary circulation.

Even in the most skilled hands, dilation of an arterial obstruction is currently not achievable in approximately 20% of attempts. The most common cause of failed PTA is the inability to pass either the guide wire or dilating catheter through the site of a tight or eccentric stenosis. This problem is even more common in attempts to dilate the difficult to access right and circumflex coronary arteries. Although technical advances, such as steerable catheters, have reduced the frequency of unsuccessful attempts, inability to cross a tight, eccentric or fully closed stenosis remains a major limitation of PTA.

Attempts at balloon or guide wire passage in vessels which are tightly stenotic may lead to arterial dissection and/or acute occlusion necessitating emergency vascular surgery. This major complication occurs in 6–8% of attempts at coronary angioplasty.

Inability to dilate an obstruction, even after proper balloon positioning and inflation is a second common mode of PTA failure. This problem is most frequently encountered in older plaques which are densely fibrotic and/or calcified.

Restenosis of the obstructed arterial segment following successful PTA is a major problem with the current technique. This problem is more common following PTA of a coronary obstruction (30–35% at one year) than in the peripheral circulation (10–15% at two years). Pharmacologic attempts to reduce the incidence of restenosis have been largely unsuccessful.

Distal embolization of atherosclerotic plaque following balloon PTA occurs in approximately 5% of patients undergoing PTA of lower extremity or renal arteries. Although these emboli are usually clinically insignificant in these vascular territories, such embolization could be catastrophic in the cerebral circulation. For this reason, balloon PTA is considered to be contraindicated for the treatment of obstructive lesions in the arteries of the aortic arch, such as the carotid artery.

In U.S. Pat. No. 4,207,874 (dated June 17, 1980) D. S. J. Choy describes a means for using a laser beam to tunnel through an arterial occlusion by vaporization of the obstruction. The difficulty with Choy's invention is that that there is insufficient means to prevent simultaneous destruction of the arterial wall. For example, the Choy invention shows an intense laser beam directed in the forward direction without significant beam attenuation in that direction. If the artery were to curve and the arterial wall was exposed to the laser beam, the wall could also be vaporized which could be catastrophic for the patient. Although the Choy invention describes a means for direct visualization of the obstructed region, it does not describe a centering means or a guide wire following means in order to guarantee that the laser beam does not illuminate part of the arterial wall. Furthermore, the Choy invention may completely obstruct a partially obstructed artery thereby cutting off blood flow to distal tissues for a significant time period. The result is ischemia which could cause irreparable damage to heart or brain tissue. Furthermore, if laser oblation was used in the carotid arteries, the resulting gas bubble formation would undoubtedly cause some cerebral ischemia resulting in permanent brain damage.

In U.S. Pat. No. 4,273,128 (date June 16, 1981) B. G. Lary describes a "Coronary Cutting and Dilating Instrument" used for opening a coronary stenosis that is restricting blood flow. The device described by Lary could not be used in a completely or nearly completely occluded artery because its "blunt ovoid tip" could not pass through a completely occluded vessel. Furthermore, the Lary invention does not have any means to prevent its cutting blade from cutting through the arterial wall as well as occluding the stenotic material. Furthermore, there is no means taught in the Lary patent for centering the cutting blade within the arterial walls. Thus, if the probe wire 13 (of FIG. 10) of the Lary invention guides the knife through a highly eccentric lumen within the stenotic plaque its knife blade would surely cut through the arterial wall which would have serious adverse effects for the patient.

In a prior patient application Ser. No. 874,140 filed on June 13, 1986, by Robert E. and Tim A. Fischell which is entitled "A Guide Wire Following Tunnelling Catheter System for Transluminal Arterial Angioplasty" there is described a means for removing stenotic plaque by advancing a tunneling catheter through a guiding catheter and around a guide wire. In that prior invention, the cutting is done by advancing the cutting catheter in a forward (anterograde) direction. A potential difficulty in such a procedure is the inability to exert enough forward force to cut through a hard calcified plaque. Furthermore, if the tunneling catheter is advanced too far in the forward direction, it could cut the arterial wall. Even with the use of cutting (as opposed to fracturing the plaque which occurs with balloon dilation) there would still be the possibility of some particulate matter flowing into the bloodstream which could result in some distal ischemia.

It is the goal of the present invention to eliminate the numerous shortcomings of the prior art in order to provide a device which can safely tunnel a clean hole through virtually any arterial stenosis without the possibility of cutting the arterial wall or creating gas bubbles, or causing the release of particulate matter into the bloodstream.

SUMMARY OF THE INVENTION

The Pullback Atherectomy Catheter (PAC) described herein operates by first penetrating the stenotic plaque in a forward direction with a conically pointed metal tip and then pulling the tip back in a retrograde direction (which tip includes a cylindrical cutting edge) to shave off a cylindrical layer of the plaque. Thus, the force required to perform the cutting is exerted by pulling back on the catheter (a retrograde motion) as opposed to the prior art devices which all cut with a forward (anterograde) motion. Sequentially larger diameter tips are progressively used to enlarge the lumen of the stenotic plaque. PAC devices would typically be guided to the stenosis by a guide wire that is first passed through the narrowed lumen. Each of the sequentially larger tips is first advanced within a guiding catheter through the stenotic plaque, then it is pulled back through the plaque to shave off plaque and finally it is withdrawn from the body. Each tip includes a chamber designed to collect the shaved off plaque thus preventing it from entering the bloodstream. Since it is virtually impossible with this technique to cause the release of particulate matter into the bloodstream, the PAC is particularly well suited for treatment of the carotid arteries.

As described in the prior application Ser. No. 874,140, which is incorporated herein by reference, one could enhance the cutting action by rotating the blade, or by applying a high energy ultrasonic vibration to the cutting edge or possibly by the application of an electrocautery current applied at the cutting edge. For PAC these means for cutting enhancement would be applied during pullback.

Thus an object of the present invention is to safely remove stenotic plaque material by first advancing the PAC tip through the stenotic lumen and then to shave off stenotic plaque by pulling back the sharpened cylindrical edge at the center of the tip through the stenosis.

Another object of the present invention is to collect the shaved off plaque into a plaque collection chamber within the tip and then remove the entire PAC including the plaque from the body.

Still another object of the present invention is to enhance the cutting action of the sharpened cylindrical edge by rotating it during pullback.

Still another object of the present invention is to utilize ultrasonic vibration of the cylindrical cutting edge to facilitate its ability to cut through the plaque.

Still another object of the present invention is to utilize an electrocautery electric current at the cylindrical cutting edge of the PAC tip to enhance its ability to cut through the plaque.

Still another object of the present invention is to use sequentially larger diameter tips each sequentially pulled back through the stenotic plaque to progressively enlarge the lumen of the stenosis.

Still another object of the present invention is to first use the PAC to bore a tunnel into the plaque and then use balloon angioplasty to further enlarge the lumen of the stenotic plaque.

Still another object of the present invention is to use the PAC system to remove plaque deposited at a branch point of an artery, i.e., to open an ostial stenosis.

Still another object of the present invention is to use the PAC to remove thrombotic tissue from an artery.

Still another object of the present invention is to apply this technique to any stenotic or occluded artery including the coronary arteries, the carotid artery, the renal, iliac or hepatic arteries and the arteries of the arms and legs.

DETAILED DESCRIPTION OF THE INVENTION

Figure 1:
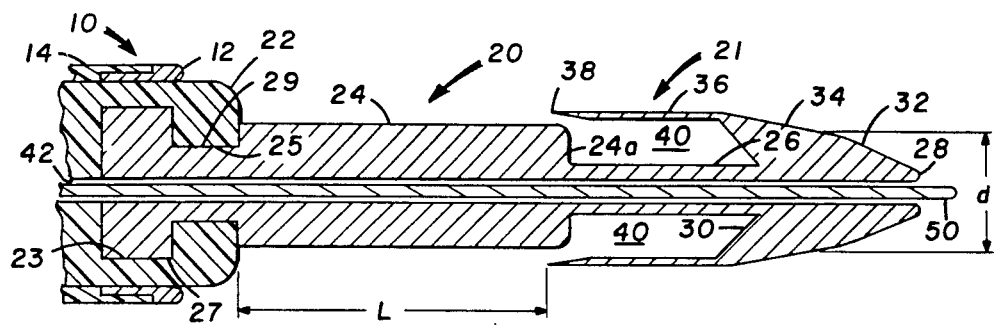
FIG. 1 is a cross-sectional view of the distal portion of the Pullback Atherectomy Catheter System.

FIG. 1 is a cross-sectional view of the distal end of the Pullback Atherectomy Catheter (PAC) System, which system consists of the PAC 20 guiding catheter 10 and guide wire 50. The guiding catheter 10 which is percutaneously or intraoperatively advanced through the arterial system has at its distal end a rigid end piece 12 joined to a plastic cylinder 14. The proximal end of the guiding catheter 10 extends outside the body. The rigid end 12 would typically be made from a metal such as steel so that it would accurately maintain its circular cross section, and the plastic cylinder 14 typically would be PVC or a similarly strong plastic material. They would typically be joined with a tight press fit or adhesive.

Contained within the guiding catheter 10 is the Pullback Atherectomy Catheter (PAC) 20 whose catheter cylinder 22 extends to outside the body at its proximal end. The PAC 20 has a metal tip 21 that is shaped so as to be easily advanced through an arterial stenosis and then to shave off the plaque material is it is pulled back through that stenosis. The metal tip 21 has at its center a guiding cylinder 24 whose outer diameter is approximately the same dimension as the interior diameter of the narrowed lumen in the stenosis. The purpose of the guiding cylinder 24 is to prevent cocking of the cutting edge 38 of the tip 21 as it is pulled back through the stenosis. The back end of the tip 21 is rigidly joined to the cylinder 22 by means of a back flange 23 and an indentation 25 of the tip 21 that are adhesively or mechanically joined respectively to the larger internal diameter 27 and smaller internal diameter 29 of the plastic cylinder 22. This construction (as shown in FIG. 1) precludes the possibility that the tip 21 will slip off the cylinder 22 during the atherectomy procedure.

As shown in FIG. 1, a connecting cylinder 26 connects the guiding cylinder 24 to the most distal portion of the tip 21. A rounded point 28 allows ready entry of the tip 21 into the stenotic lumen whose diameter "d" is approximately equal to the outer diameter of the guiding cylinder 24. Going backward from the point 28, is a conical surface 32 which has a comparatively steep slope. At a distance just slightly less than the stenotic lumen diameter "d", the shape of the tip 21 changes to a conical surface 34 which has a very shallow slope. The purpose of this shallow slope is to allow a decreased forward force when pushing the tip 21 through the stenotic lumen. The purpose of the comparatively steep slope of the conical surface 32 is to provide a shorter length for the tip 21 so that it can more easily pass through a curved arterial lumen. It should be understood, however, that one could use a single conical surface at the front of the tip 21, especially for tips that have a very small diameter. For example, the smallest outer diameter of the cutting cylinder 36 of the tip 21 might be 1.0 mm (40 mils). For that small a diameter, only a single, comparatively shallow slope of the conical surface would be needed because, for that small diameter, the length of the tip 21 would be quite short enough to pass through even a highly curved arterial lumen.

Returning again to FIG. 1, the cutting cylinder 36 has a sharpened edge 38. The purpose of the sharpened edge 38 is to shave off plaque material as the tip 21 is pulled backward just as a wood plane would shave a piece of wood. The thickness of the cutting cylinder 36 would typically be between 2 and 5 mils. The difference in diameter between the outer diameter of the guiding cylinder 24 and the diameter of the cutting edge 38 would typically be between 0.25 mm and 2 mm, (i.e. between 10 and 80 mils). At a typical diameter difference of 0.5 mm, a radial shaving of 0.25 mm (10 mils) thickness would be shaved off as the tip 21 is pulled back through the stenosis. Thus, a succession of PACs 20 whose tips 21 would have sequentially increasing diameters would be needed to increase the diameter of the stenotic lumen from, let us say, a minimum of 1.0 mm diameter to a maximum of let us say 5.0 mm. Each of these stages in the atherectomy procedure might increase the luminal diameter of the stenotic plaque by approximately 0.5 mm. By using staged tips 21 of successively increasing diameter, the thrust required to force the conical surface 34 in a forward direction through the stenotic lumen is always kept to a very low value. The reasons why this force can be kept very small are as follows:

(1) the lumen does not have to be enlarged very much in each stage (typically only 0.5 mm in diameter),
(2) the slope of the conical surface is very shallow,
(3) the conical surface 34 is polished so that it is very smooth, and
(4) the blood acts as a lubricant between the polished metal conical surface 34 and the plaque which, when combined with the polished finish of the metal, results in a very low coefficient of friction.

It should be noted that coating the exterior surface of the tip 21 with Teflon could further reduce the force required to push the PAC 20 through the stenosis.

Returning again to FIG. 1, the volume enclosed by the interior surface of the cutting cylinder 36, the outer surface of the connecting cylinder 26, the most distal surface 24a of the guiding cylinder 24 and the interior conical surface 30 forms a plaque collection chamber 40. As the plaque is shaved from the interior surface of the stenotic lumen, it is collected in the chamber 40 and is removed from the body when the PAC 20 is removed from the body.

At the center of the catheter cylinder 22 and the tip 21 of the PAC 20 is a passageway 42 through which a guide wire 50 can be inserted. The guide wire 50 is used to first penetrate the narrow stenotic lumen and is then used to guide the tip 21 through that same lumen. If a radial hole (not shown in FIG. 1) was made in the connecting cylinder 26, the application of a suction through the passageway 42 could be used to assist in keeping the shaved plaque within the chamber 40.

The passageway 42 can also be used for injecting angiographic dye to the site of the stenosis and for flushing out that passageway 42 with saline solution.

Returning again to FIG. 1, the distance "L" would typically be just slightly longer than the length of the stenosis where it is in contact with the tip 21. The length of the cutting cylinder 36 would typically be between ½L and 2L in length. Typical values of L would be between 5 and 20 mm.

The material of the tip 21 would typically be any steel which could be sharpened to a very sharp edge. Thus steels such as those used for razor blades or surgical scalpels would be best suited for this purpose.

Figure 2:
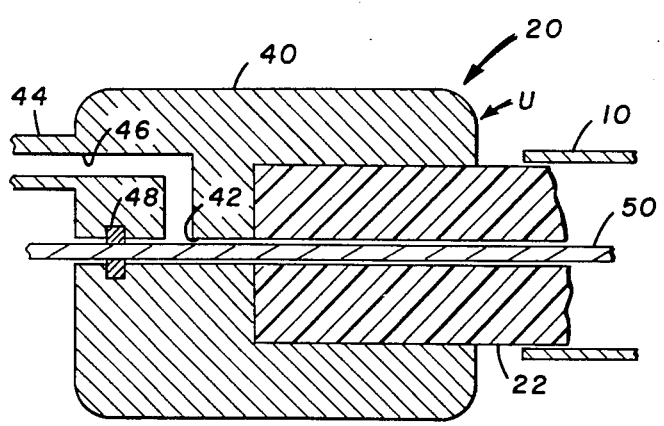
FIG. 2 is a cross-sectional view of the proximal portion of the Pullback Atherectomy Catheter System.

FIG. 2 is a cross-sectional view of the proximal end of the PAC 20 which lies outside the body, typically near the patients thigh where the PAC 20 is percutaneously inserted through the femoral artery. The guiding catheter 10 whose interior surface is typically sealed against the outer surface of the catheter cylinder 22 is also typically equipped with a means for injecting liquids such as angiographic dye and/or saline flushing solution. These capabilities are well known in the art of percutaneous transluminal angioplasty, so they have not been illustrated herein. The catheter cylinder 22 is typically adhesively joined to a metal or plastic handle 40 as is shown in FIG. 2. The metal used for the handle might be stainless steel and the plastic might be acetal or PVC or a similar material. The guide wire 50 is sealed into the handle 40 by an elastomer seal 48 which may typically be made of silicon rubber. The handle includes an inlet port 44 whose interior passageway 46 is in fluid communication with the passageway 42. Angiographic dye or a rinsing saline solution that is injected into the passageway 46, would then go through the passageway 42 and would finally emerge from the distal end of the tip 21. If there was a radial hole in the connecting cylinder 26 of FIG. 1 that allowed fluid communication between the passageway 42 and the plaque collection chamber 40, then the application of a suction to the passageway 46 would result in a suction in the plaque collection chamber 40. Such a suction would be enhanced if the passageway 42 was made to be a tight sliding fit around the guide wire 50 at the extreme distal end of tip 21. An ultrasonic vibratory energy source U, if applied at the distal end of the handle 40 as shown in FIG. 2, could assist in the cutting action of the plaque as the cutting edge 38 (of FIG. 1) is pulled back through the stenosis. Such a vibratory source U would undoubtedly also be effective if applied at the proximal end of the handle 40.

Figure 3:
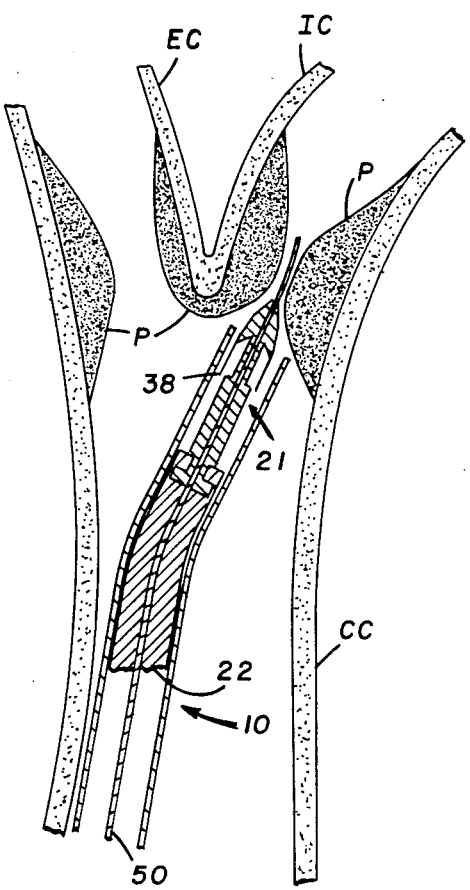
FIG. 3 is a cross-sectional view of the carotid artery showing the Pullback Atherectomy Catheter System in place just proximal to a stenotic plaque.

FIG. 3 shows typical plaque deposits in the carotid arteries. This plaque P is typically deposited in the external carotid artery EC, the internal carotid artery IC and the common carotid artery CC as is generally illustrated in FIG. 3. The internal carotid IC provides blood to the brain. An important object of the PAC System is to restore adequate blood flow without a surgical procedure.

Figure 6:
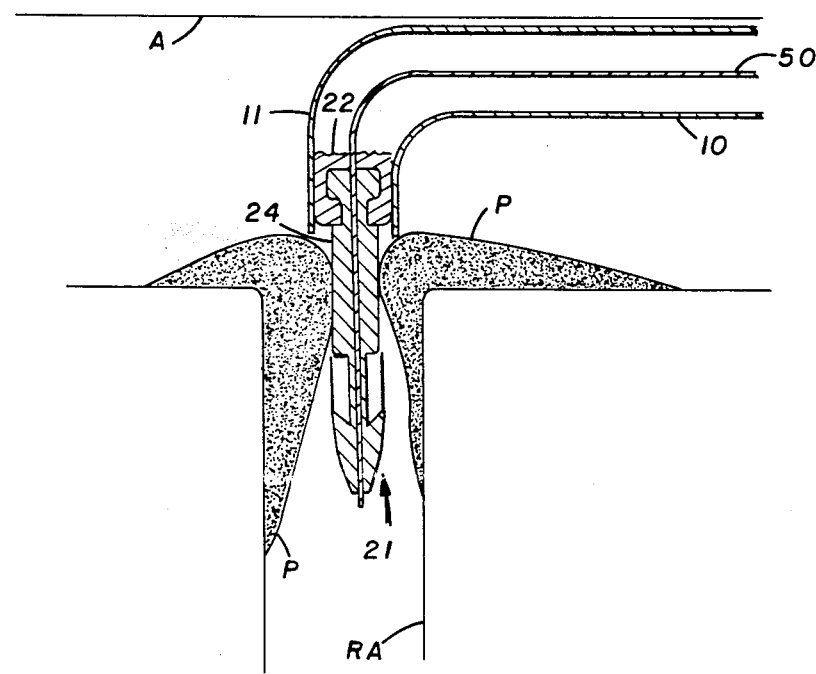
FIG. 6 shows the cross section of the Pullback Atherectomy Catheter System after the PAC tip has been advanced through an ostial stenosis in the renal artery.

FIG. 3 shows a guiding catheter 10 that has been percutaneously inserted typically through the femoral artery and subsequently advanced to be just proximal to the stenosis in the internal carotid artery IC. The physician would then advance a guide wire 50 through the center of the PAC 20 (of FIGS. 1 and 2) and then would advance that assembly until its distal end was positioned as shown in FIG. 3. The catheter cylinder 22 would then be thrust forward causing the tip 21 to be pushed through the stenotic lumen until the cutting edge 38 was just forward of the stenotic lumen (as is shown in FIG. 6 for the renal artery). By means of the handle 40 of the PAC 20 (see FIG. 2) the tip 21 would then be pulled back through the stenosis (as shown in FIG. 4) and a cylindrical section of plaque would be removed.

Figure 4:
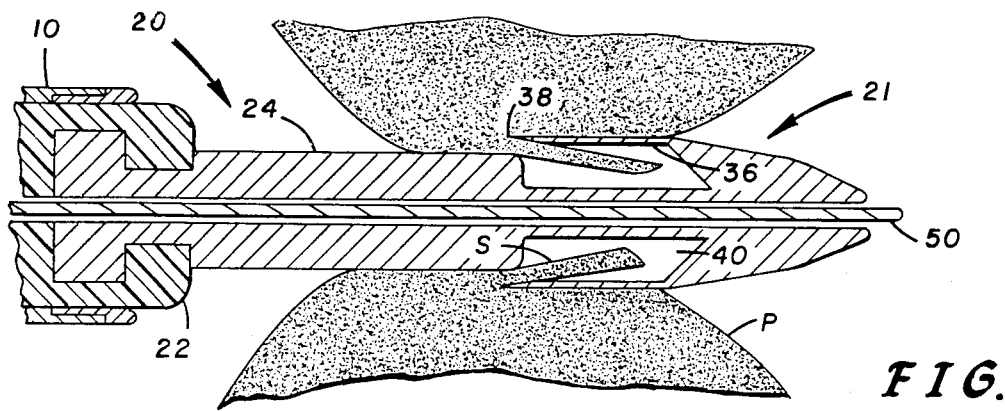
FIG. 4 is an enlarged cross-sectional view showing the Pullback Atherectomy Catheter being pulled back through the stenotic plaque.

FIG. 4 is an enlarged cross-sectional view of the tip 21 of the PAC 20 as it is pulled back through the plaque P which forms a stenosis. We see in FIG. 4 that the sharpened edge 38 has shaved off a plaque shaving S and is depositing that shaving S into the plaque collection chamber 40. If necessary, the volume of the chamber 40 could be enlarged by hollowing out the guiding cylinder 24 or by making a longer cutting cylinder 36.

The tip 21 is first pulled back completely into the guiding catheter 10, and then it is completely removed from the body with the plaque securely contained within the plaque collection chamber 40. Thus the plaque should be able to be removed without causing particulate matter to be placed in the bloodstream.

For the first used and smallest diameter tip 21, the guiding cylinder 24 would be approximately equal to or slightly larger than the interior diameter of the stenotic lumen. Once that smallest tip 21 was successfully pulled back through the stenosis, the next larger diameter tip 21 would be used. Typically the sequentially larger diameter of the tip 21 would have the diameter of its guiding cylinder 24 equal to the outer diameter of the cutting cylinder 36 of the prior tip 21. Three to six sequentially larger diameter tips 21 might be used to expand the narrowed passageway in the stenosis from as little as 1 mm in diameter to as much as 5 mm. The largest tip 21 would have an outer diameter of its cutting cylinder 36 that just fits within the interior diameter of the guiding catheter 10.

Figure 5:
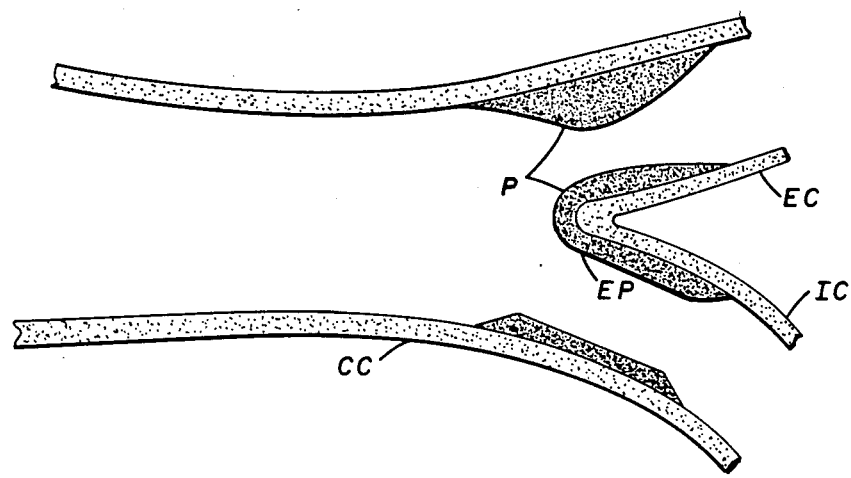
FIg. 5 shows the cross section of the stenotic plaque in the carotid artery after atherectomy has been completed.

FIG. 5 shows the enlarged passageway EP that has been formed in the stenosis after the largest tip 21 was pulled back and after the guide wire 50 and the guiding catheter 10 were removed from the body.

Although this procedure was described specifically for the carotid artery, it is readily applicable to any stenosis of an artery in the body. For example the PAC System could be used to open stenoses in the coronary, iliac, renal or hepatic arteries or in any other peripheral artery in the arms or legs or elsewhere. The PAC System could also be used to remove deposits in by-pass vein grafts and to remove thrombus from arteries or veins. The PAC System might ideally be applied for removing both thrombus and plaque from a coronary artery in the early treatment of myocardial infarction.

A particular stenosis that is not readily opened by balloon angioplasty is one that is at the branch point of an artery. This particular type of narrowing is called an ostial stenosis. One such arterial stenosis, illustrated in FIG. 6, shows the lumen of the aorta A joining to the lumen of the renal artery RA with plaque deposits P that form an ostial stenosis. Also shown in FIG. 6 is the PAC tip 21 after it has been advanced through the stenosis just prior to pullback. Here we see the outer diameter of the guiding cylinder 24 being just equal to (or slightly larger than) the diameter of the lumen of the stenosis. Prior to achieving the position shown in FIG. 6, the guide wire 50 was advanced through the narrowed passageway in the lumen. Furthermore, the tip 21 and the catheter cylinder 22 were both advanced percutaneously within the guiding catheter 10 to the position shown in FIG. 6. The distal end 11 of the guiding catheter 10 would have a preformed shape as shown in cross section in FIG. 6 so as to enhance the entry and pullback of the tip 21 into and out of the ostial stenosis. Again sequentially larger diameter tips 21 would be used until a sufficiently large luminal diameter would be formed to allow adequate blood flow to the kidney.

Wherever in the body the PAC System is used, the tip 21 can be pushed through and pulled back from the stenosis in a matter of 5 to 30 seconds. Although blood flow to a distal organ (such as the brain or kidney) would be stopped during that time period, even the longest time period of 30 seconds would not result in damage to any tissue due to ischemia.

As described in the referenced prior application Ser. No. 874,140, the handle 40 (of FIG. 2) could be rotated during the cutting process to enhance the cutting action of the cutting edge 38 of FIGS. 1 and 4. Also, if the entire tip except for the cutting edge 38 was electrically insulted (e.g., with Teflon) then an electrocautery current applied to the tip (as described in the above referenced patent application) would enhance the cutting action of the cutting edge 38 as the tip 21 is pulled back through the stenosis. To accomplish this, the catheter cylinder 22 must contain an electrical conductor that would electrically connect the tip 21 to a metal handle 40. Then one end of an electrocautery current generator would be electrically attached to the handle 40. A grounding plate attached to the patient would be joined to the ground terminal of the electrocautery generator.

Another method to enhance the cutting action during pullback would be to provide the cutting edge 38 with a serrated edge similar to that which is used for bread knives. Then when the tip 21 is rotated as it is pulled back, there would be a more effective cutting of the plaque.

Although the present invention has only described the removal of plaque or thrombus from human arteries, the PAC could also be used to remove other stenotic or occluding tissue from ducts such as the ureters or the fallopian tubes. The PAC might also be useful in cleaning vessels of various animals.

Although percutaneous PAC procedures are for the most part described herein, large tip diameters could be used intraoperatively by surgical incision into a major artery.

One possible additional use of the PAC System might be as a precursor to balloon dilation. A balloon catheter angioplasty procedure could be used to further enlarge a stenotic lumen after the smallest diameter PAC tip 21 had provided an initial luminal enlargement.

Various other modifications, adaptations, and alternative designs are, of course, possible in light of the above teachings. Therefore, it should be understood at this time that within the scope of the appended claims, the invention may be practiced otherwise than as specifically described herein.

What is claimed is:

1. An atherectomy apparatus comprising:
   a member having a distal portion adapted to be advanced through an obstructed arterial lumen, said member including,
   a cylindrical cutting blade means having a cutting edge facing toward the proximal end of said apparatus for cutting obstructive material as said member is pulled back through said lumen; and,
   a means for securing the cut material within a collection chamber that is integrally formed within said cutting blade means, whereby removed material is retained without the cooperation of a second member requiring motion relative to said cutting blade means, and wherein said means for securing cut material within said collection chamber comprises a shoulder portion positioned in cooperation with said cutting blade means to form therebetween a restricted entrance mouth to said collection chamber, so as to retain cut material in said collection chamber.

2. The apparatus of claim 1, wherein said shoulder portion is a cylindrical form, and wherein the outer diameter of a distal region of said cylindrical form is slightly smaller than the diameter of said cutting blade means, so as to form said restricted entrance mouth therebetween.

3. An atherectomy apparatus, comprising:
   a member having a distal portion adapted to be advanced through an obstructed arterial lumen, said member including,
   a cylindrical cutting blade means having a cutting edge facing toward the proximal end of said apparatus for cutting obstructive material as said member is pulled back through said lumen; and,
   a means for securing the cut material within a collection chamber that is integrally formed within said cutting blade means, whereby removed material is retained without the cooperation of a second member requiring motion relative to said cutting blade means, and wherein said member includes an interior passageway that is adapted to fit around a guide wire so that said member can be advanced along said guide wire.

4. An atherectomy apparatus, comprising:
   a member having a distal portion adapted to be advanced through an obstructive arterial lumen, said member including,
   a cylindrical cutting blade means having a cutting edge facing toward the proximal end of said apparatus for cutting obstructive material as said member is pulled back through said stenotic lumen;
   a means for securing the cut material within a collection chamber that is integrally formed within said cutting blade means, whereby removed material is retained without the
   cooperation of a second member requiring motion relative to said cutting blade means; and,
   an ultrasonic means operably coupled to said distal portion for causing vibratory motion of said distal portion.

5. An atherectomy apparatus comprising:
   a distal portion adapted to be advanced through an arterial stenotic lumen;
   a cylindrical cutting blade having a circular cutting edge facing toward the proximal end of said apparatus for cutting stenotic material as said circular cutting edge is pulled back through stenotic lumen, said circular cutting edge having a first and largest diameter;
   a hollow chamber formed within said apparatus between said cylindrical cutting blade and a cylindrical inner portion of said distal member having a second and smallest diameter; and,
   a second guide portion fixedly attached at its distal end to the proximal end of said cylindrical inner portion, having a third and intermediary diameter larger than said second diameter but less than said first diameter and cooperating with said cylindrical inner portion and said cylindrical cutting blade to form a hollow collection chamber having a restricted entrance mouth, so as to retain the cut stenotic material in said hollow chamber.

6. The apparatus of claim 5, wherein the distal end of said distal portion is shaped so as to include a forward guiding means for guiding said member as it is advanced through said stenotic lumen.

7. The apparatus of claim 6, wherein said forward guiding means has a conically shaped surface.

8. The apparatus of claim 7, wherein said conically shaped surface has at least two different slopes.

9. The apparatus of claim 5, wherein said circular cutting edge is serrated so that rotation of said circular cutting edge will enhance cutting during pullback.

10. The apparatus of claim 5, wherein said apparatus is operably connected to a catheter cylinder having a proximal end extending external to said living body.

11. The apparatus of claim 10, wherein said catheter cylinder and said apparatus contains an internal passageway so that fluid can be injected through said internal passageway to the site of said stenotic lumen.

12. The apparatus of claim 5, further comprising a means for rotating said distal portion as said apparatus is pulled back through the stenotic lumen.

13. An atherectomy apparatus comprising:
   a guide wire adapted to be advanced in an antegrade direction so as to penetrate through an obstructed arterial lumen;
   a member having a distal portion adapted to be advanced through said obstructed arterial lumen, said member having an inner lumen adapted to fit around said guide wire so that said distal portion can be advanced along said guide wire; and said member including,
   a removing means having a cutting blade facing toward the proximal end of said member and a collection chamber integrally formed within said cutting blade for cutting and collecting obstructive material as said cutting blade is pulled back through said arterial lumen.

14. The apparatus of claim 13, wherein said cutting blade has a circular cutting edge and wherein said removing means collects obstructive material without the cooperation of a second member requiring motion relative to said cutting blade.

15. The apparatus of claim 13, wherein said cutting blade is serrated.

16. The apparatus of claim 13, further comprising a means for rotating said distal portion as said apparatus is pulled back through said obstructed arterial lumen.

17. The apparatus of claim 5, wherein the exterior surface of said distal portion is polished to reduce its coefficient of friction.

18. The apparatus of claim 5, wherein the exterior surface of said distal portion is coated with a substance to reduce its coefficient of friction.

19. The apparatus of claim 18, wherein said exterior surface is coated with Teflon.

20. The apparatus of claim 5, wherein said cutting edge is made from a hard metal sharpened to form a sharp cutting edge.

21. An atherectomy catheter, comprising:
   a catheter having a distal portion adapted to be advanced through a stenotic lumen in a tubular vessel of a living body, said distal portion comprising,
   a cutting cylinder having a sharpened edge, said sharpened edge facing toward the proximal end of said catheter tip for removing stenotic material as said distal portion is pulled back through said stenotic lumen;
   a guiding cylinder located at the proximal end of said distal portion for guiding said distal portion as it is pulled back through said stenotic lumen, said guiding cylinder having an outer diameter slightly less than the diameter of said sharpened edge, so that a gap is formed therebetween;
   a conical guiding surface located at the distal end of said distal portion for guiding said distal portion as it is advanced through said stenotic lumen;
   a hollow chamber formed within said distal portion, wherein the gap formed between said sharpened edge and said guiding catheter forms the mouth to said hollow chamber so that said hollow chamber will collect stenotic material removed from the interior of said stenotic lumen;
   an inner passageway running the length of said catheter and said distal portion, said passageway adapted to fit around a guide wire so that said distal portion can be advanced along said guide wire.

22. The catheter of claim 21, wherein the outer diameter of said guiding cylinder is approximately the diameter of the narrowed stenotic lumen.

23. The catheter of claim 21, wherein said conical guiding surface has a front portion having a relatively steep conical slope and a back portion having a relatively shallow slope.

24. The catheter of claim 21, wherein the outer surface of said cutting cylinder is treated to reduce its coefficient of friction.

25. The catheter of claim 21, wherein said gap formed between said sharpened edge and said guiding cylinder measures 10 to 80 mils.

26. The catheter of claim 21, wherein said sharpened edge is serrated so that rotation of said distal portion will enhance cutting action of the sharpened edge.

27. A method for removing obstructive material from an artery in a living body, comprising the steps of
   advancing a guide wire so that its distal end extends beyond an arterial obstruction,
   advancing the distal portion of an atherectomy catheter along the guide wire and beyond the obstruction;
   pulling back said atherectomy catheter thereby causing a cutting edge that faces toward the proximal end of said atherectomy catheter and forms the mouth of a collection chamber to both cut and collect obstructive material into said collection chamber during the same single pullback motion.

28. The method of claim 27 further including the step of rotating said cutting edge during said pull back step.

29. A method for improving arterial blood flow by:
   percutaneously passing a guiding catheter forward through the arterial system of a living body until its distal end is proximal to a stenosis;
   deploying a guide wire and a pullback atherectomy catheter by advancing the guide wire until the distal end of the guide wire passes through the stenotic lumen and advancing the distal portion of the pullback atherectomy catheter to a position just proximal to the stenosis;
   advancing the pullback atherectomy catheter through the stenotic lumen; and,
   pulling said catheter back through said stenotic lumen thereby causing a cutting edge that faces toward the proximal end of said catheter to remove stenotic material.

30. The method of claim 29, further comprising the steps of:
   collecting the removed material from the stenosis in a hollow chamber formed within said distal portion of said pullback atherectomy catheter, said hollow chamber having an opening beneath said cutting edge; and
   removing said pullback atherectomy catheter with stenotic material from said living body.

31. The method of claim 29, wherein said deploying step involves first advancing said guide wire through the stenotic lumen and then advancing the pullback atherectomy catheter along said guide wire.

32. The method of claim 29, wherein said deployment involves first assembling said guide wire in said pullback atherectomy catheter and then advancing the assembly through said guiding catheter.

33. The method of claim 29, wherein said pullback atherectomy catheters include said distal portions of progressively larger diameter which are used for progressively increasing the area of the stenotic lumen.

34. The method of claim 29, wherein the distal end of said guiding catheter is given a preformed shape to suit a particular arterial geometry.

35. The method of claim 29, further comprising the step of employing an angioplasty balloon catheter procedure to further dilate the stenotic lumen.

36. An atherectomy apparatus, comprising:
   a member having a distal portion adapted to be advanced through an obstructive arterial lumen, said member including,
      a cylindrical cutting blade means having a cutting edge facing toward the proximal end of said apparatus for cutting obstructive material as said member is pulled back through said lumen;
      a means for securing the cut material within a collection chamber that is integrally formed within said cutting blade means, whereby removed material is retained without the cooperation of a second member requiring motion relative to said cutting blade means; and,
   an electrocautery cutting means having an electrical current means electrically grounded to said living body and also having a second connection to said distal portion for enhancing removal of obstructive material.

* * * * *